United States Patent
Luong et al.

(10) Patent No.: US 10,214,596 B2
(45) Date of Patent: Feb. 26, 2019

(54) CHITIN NANOCRYSTALS AND PROCESS FOR PREPARATION THEREOF

(71) Applicant: National Research Council of Canada, Ottawa (CA)

(72) Inventors: John H. Luong, Mont Royal (CA); Edmond Lam, Montreal (CA); Chi Woon Leung, Hampstead (CA); Sabahudin Hrapovic, Laval (CA); Keith B. Male, Kirkland (CA)

(*) Notice: Subject to any disclaimer, the term of this patent is extended or adjusted under 35 U.S.C. 154(b) by 44 days.

(21) Appl. No.: 15/036,080

(22) PCT Filed: Nov. 12, 2014

(86) PCT No.: PCT/CA2014/051084
§ 371 (c)(1),
(2) Date: May 12, 2016

(87) PCT Pub. No.: WO2015/070346
PCT Pub. Date: May 21, 2015

(65) Prior Publication Data
US 2016/0272731 A1    Sep. 22, 2016

Related U.S. Application Data

(60) Provisional application No. 61/905,403, filed on Nov. 18, 2013.

(51) Int. Cl.
| | | |
|---|---|---|
| C08B 37/00 | (2006.01) | |
| C30B 29/58 | (2006.01) | |
| C08B 37/08 | (2006.01) | |
| C30B 7/00 | (2006.01) | |
| C30B 29/60 | (2006.01) | |
| C30B 1/10 | (2006.01) | |

(52) U.S. Cl.
CPC ........ *C08B 37/0003* (2013.01); *C08B 37/003* (2013.01); *C30B 1/10* (2013.01); *C30B 7/00* (2013.01); *C30B 29/58* (2013.01); *C30B 29/60* (2013.01); *C07B 2200/13* (2013.01)

(58) Field of Classification Search
None
See application file for complete search history.

(56) References Cited

U.S. PATENT DOCUMENTS

| 4,931,551 A | 6/1990 | Albisetti et al. |
|---|---|---|
| 6,303,046 B1 * | 10/2001 | Risen, Jr. ................. B01J 20/02 |
| | | 106/162.2 |
| 2010/0260845 A1 * | 10/2010 | Jayakrishnan ....... A61K 9/0014 |
| | | 424/484 |
| 2012/0244357 A1 | 9/2012 | Leung et al. |

FOREIGN PATENT DOCUMENTS

| JP | S59113185 | 6/1984 |
|---|---|---|
| RU | 2256601 | 7/2005 |
| WO | 2011/072365 | 6/2011 |

OTHER PUBLICATIONS

Ghosh, D., Pramanik, A., Sikdar, N., Ghosh, S. K., & Pramanik, P. (2010). Amelioration studies on optimization of low molecular weight chitosan nanoparticle preparation, characterization with potassium per sulphate . . . Int J Pharm Sci Drug Res, 2(4), 247-253. (Year: 2010).*
International Search Report and Written Opinion on PCT/CA2014/051084 dated Jan. 20, 2015.
Abstract of Bragd et al. Topics in Catalysis. (2004) 27(1-4), 49-66.
Fan Y., et al. Biomacromolecules. (2008) 9, 192-198.
Abstract of Goodrich, JD, et al. Biomacromolecules. (2007) 8(1), 252-257.
Abstract of Leung ACW, et al. Small. (2011) 7(3), 302-305.
Abstract of Sun Q, et al. Carbohydr Palm. (2014) 106, 359-64.
Oun AA, et al. Effect of isolation methods of chitin nanocrystals on the properties of chitin silver hybrid nanoparticles. Carbohydrate Polymers. 197 (2018) 349-358.

* cited by examiner

*Primary Examiner* — Shaojia A Jiang
*Assistant Examiner* — Dale R Miller
(74) *Attorney, Agent, or Firm* — Brunet & Co. Ltd.; Robert Brunet; Hans Koenig

(57) ABSTRACT

A process for producing chitin nanocrystals (ChNCs) involves contacting a chitinous material with a sufficient amount of an inorganic persulfate to produce chitin nanocrystals from the chitinous material. The process permits one-spot production of ChNCs from biomasses such as crustaceans, fungi, mushrooms, insects or mixtures thereof. Chitin nanocrystals produced by the process comprise surface carboxylic groups and are not initially deacetylated.

20 Claims, 10 Drawing Sheets

CHITIN NANOCRYSTALS AND PROCESS FOR PREPARATION THEREOF

CROSS-REFERENCE TO RELATED APPLICATIONS

This application is a national entry of International Patent Application PCT/CA2014/051084, filed Nov. 12, 2014 and claims the benefit of U.S. Provisional Patent Application Ser. No. USSN 61/905,403 filed Nov. 18, 2013, the entire contents of both of which are herein incorporated by reference.

FIELD

This application relates to a process for producing chitin nanocrystals (ChNCs) from biomass, and to chitin nanocrystals comprising carboxylic groups produced by the process.

BACKGROUND

The two most abundant and renewable biomaterials in nature, cellulose and chitin, are chemically similar, semi-crystalline, and both form natural hierarchical composites. Similar to the role of cellulose in trees and plants, chitin serves as a major component in the supporting tissues of crustaceans, fungi, mushrooms, insects, etc. Annual availability of chitin is about 1 to 100 billion ton (Nair 2003) with shrimp and crab wastes as the principal source of raw materials. The United Nations Food and Agricultural Organization (FAO) estimated that the global production of shrimp and crab from 1995 to 1999 was 4,021,521 and 1,299,464 ton/y, respectively, and the fisheries normally produce a crustacean waste of about 30% or about $1.6 \times 10^6$ ton/y. Although 150,000 ton/y of chitin are currently available for commercial/industrial applications, only a few thousand tons are actually used for worldwide commercial applications. As a natural substance in various foodstuffs, chitin is considered as a safe material. To date, chitin and its derivatives have shown promise in the biomedical, food, cosmetic, and textile industries due to their biocompatibility, biodegradability, antimicrobial properties, and high tensile strength. Thus, it is important to further develop efficient and widespread use of chitin as a natural and eco-friendly material.

Chitin is a linear polysaccharide, white and porous material; consisting of $\beta$-(1→4)-2-deoxy-2-acetamido-D-glucopyranose, i.e., the structure of chitin is similar to cellulose, except that the C2-hydroxyl group of cellulose is replaced by an acetamide group in chitin. The chitin molecules exhibit helicoidal and microfibrillar structures comprising nanofibers about 2-5 nm in diameter and about 300 nm in length embedded in several protein matrices (Raabe 2006). Chitin has three crystalline polymorphs, $\alpha$, $\beta$ and $\gamma$, which are organized as sheets of chitin chains held tightly by a number of strong C—O . . . H—N interchain hydrogen bonds. $\alpha$-Chitin, the most abundant form, contains alternating antiparallel chains per unit cell whereas $\beta$-chitin contains only parallel chains per unit cell. $\gamma$-Chitin has two chains running in one direction and another chain running in the opposite direction and its X-ray diffraction is very similar to that of $\alpha$-chitin (Jang 2004). Therefore, the crystalline nature of $\alpha$-chitin inhibits its solubility in most organic solvents whereas $\beta$-chitin is more susceptible to swelling, especially in aqueous media. This could be the reason why $\alpha$-chitin has limited applications despite its available abundance. Nevertheless, deacetylation of chitin leads to water-soluble chitosan, which has been more widely studied and explored for various applications (Azzaroni 2005).

Analogous to cellulose, chitin comprises both crystalline and amorphous domains and the latter can be hydrolyzed to release the crystalline segments. Cellulose nanocrystals (CNC) have received significant attention as biomaterials for diversified applications and several production methods have been established for this nanoscale material (Lam 2012; Leung 2012; Leung 2013). In contrast, there are only a few reports on the synthesis of chitin nanocrystals (ChNCs) by subjecting chitin to acid hydrolysis and mechanical disruption (Goodrich 2007; Fan 2008). Acid hydrolysis in these reports requires an expensive chemical, TEMPO ((2,2,6,6-tetramethylpiperidin-1-yl)oxyl, or (2,2,6,6-tetramethylpiperidin-1-yl)oxidanyl) to prepare oxidized chitin nanocrystals or oxidized cellulose nanocrystals obtained from acid hydrolysis. Acid hydrolysis randomly cleaves the non-crystalline regions of the microfibrils to produce stable colloidal suspensions of rod-like particles of nanoscale dimensions (Revol 1993; Li 1997). As with CNCs, $\alpha$-chitin nanocrystals have several advantageous properties, such as small size and high particle aspect ratio, high surface area, high stiffness and strength, wide availability and renewability, low density, and ease of chemical modification. Indeed, chitin may offer more design versatility over cellulose, considering the presence of both hydroxyl and amine/N-acetyl functionalities on the surface for chemical modification and conjugation.

RU 2256601 (Chvalun 2005) discloses the use of a radical initiator (e.g. potassium persulfate) for polymerization of acrylamide to polyacrylamide in the formation of nanocomposites containing chitin nanocrystals. Persulfate is only present in low concentrations of (0.1-1.0 wt %) with the reaction performed at basic pH, which is insufficient to achieve oxidation and hydrolysis of chitin. Nanocrystalline chitin is created by mechanical disintegration. JP-S59113185 (Tomoji 1984) discloses the treatment of chitin-based waste with an oxidant, one of which could be sodium persulfate, to deodorize chitin-based industrial waste. The resulting chitin is further treated with various chemicals to remove dust from used metal. Persulfate is not used for the effective hydrolysis of chitin at acidic pH and oxidation of chitin to form highly crystalline nano-chitin. U.S. Pat. No. 4,931,551 (Albisetti 1990) discloses the use of an oxidizing agent for breaking down, bleaching and dispersing chitin in an alkaline aqueous medium. The main purpose of the oxidant is the dispersion of chitin as the size of chitin remains unchanged during the course of treatment.

There remains a need for a simple effective method for producing chitin nanocrystals.

SUMMARY

In one aspect of the present invention, there is provided a process for producing chitin nanocrystals (ChNCs) comprising contacting a chitinous material with a sufficient amount of an inorganic persulfate to produce chitin nanocrystals from the chitinous material.

The inorganic persulfate preferably comprises ammonium persulfate $((NH_4)_2S_2O_8)$, sodium persulfate $(Na_2S_2O_8)$, potassium persulfate $(K_2S_2O_8)$ or a mixture thereof. More preferably, the inorganic persulfate comprises ammonium persulfate.

Any suitable source of chitinous material may be used, for example biomass, in particular non-vegetative biomass. Non-vegetative biomass may include animal sources, for example crustaceans, fungi, mushrooms, insects or mixtures thereof. Shrimp, crab and mixtures thereof are sources of particular note. The chitinous material may be provided to process directly from such sources. Advantageously, ChNCs may be produced in one-spot from such non-vegetative biomass.

The process is preferably conducted in a process mixture preferably comprising a solvent, preferably an aqueous solvent. The persulfate may be dissolved or otherwise dispersed in the solvent. A sufficient amount of persulfate is used to hydrolyze/oxidize the chitinous material to form chitin nanocrystals. The sufficient amount may be provided by a concentration of persulfate in the solvent ranging from about 0.5 M to about 2.0 M, more preferably in a range of from about 0.5 M to about 1.0 M, for example about 1.0 M. In aqueous solution, the pH of the solution is preferably acidic, more preferably below pH 4, for example pH 2. The chitinous material preferably comprises about 0.5 wt % or greater of chitin, based on total weight of the chitinous material, more preferably about 0.5 wt % to about 4 wt %, even more preferably about 0.5 wt % to about 2 wt %, yet even more preferably about 1 wt % to about 2 wt %, for example about 1 wt %. Preferably, the amount of chitin in the process mixture is in a range of from about 1 wt % to about 15 wt %, based on total weight of the process mixture. More preferably, the amount of chitin is in a range of about 1 wt % to about 14 wt %, or about 1 wt % to about 13 wt %, or about 1 wt % to about 12 wt %, or about 1 wt % to about 11 wt %, or about 5 wt % to about 10 wt %. Preferably, a ratio of the chitin to the inorganic persulfate in the process mixture is in a range of about 1:1.75 to about 1:25, more preferably about 1:2 to about 1:8, even more preferably about 1:2 to about 1:5.

The process is preferably conducted at an elevated temperature. Preferably, the elevated temperature is in a range of from about 45° C. to about 80° C., for example about 60° C. Preferably, contacting the chitinous material with persulfate is performed for a period of time in a range of from about 6 hours to about 24 hours, for example about 12 hours. Preferably, the persulfate is stirred with the chitinous material, more preferably constantly stirred.

The chitin nanocrystals may be recovered after being formed in the process. Any suitable recovery method may be used, for example, settling and decanting, filtration, centrifugation and the like.

In another aspect of the present invention, there is provided a chitin-based material comprising nanocrystals of chitin, the nanocrystals having surface carboxylic acid groups. The formation of ChNCs may occur via cleavage of glycosidic bonds and individualization of elementary fibrils by the formation of charged carboxylate groups on the surfaces of the chitin crystallites. During the persulfate treatment, selective oxidation preferably occurs at the C6 primary hydroxyl group of chitin to form carboxylic acid groups. Preferably, the degree of oxidation (DO) is in a range of from about 0.04 to about 0.20, more preferably in a range of from about 0.05 to about 0.15 or about 0.06 to about 0.15.

Nanocrystals are crystals having at least one dimension measuring 100 nm or less. In another aspect of the present invention, there is provided a chitin-based material comprising nanocrystals of chitin with an average width of about 20 nm or less. The average width is preferably about 10 nm or less. In one embodiment, the average width is in a range of from about 3 nm to about 10 nm. Preferably, substantially all of the nanocrystals have widths within about 0.3 nm of the average width. The ChNCs preferably have an aspect ratio (length/width (L/W)) of 10 or greater. The aspect ratio is preferably up to about 60, more preferably in a range of from about 12 to about 60. Preferably, substantially all of the nanocrystals have lengths within about 15 nm of the average length, more preferably within about 10 nm. The surface area of the ChNCs is high, preferably in a range of about 50-500 $m^2/g$, more preferably about 100-300 $m^2/g$. Such ChNCs may also be carboxylated as described above.

ChNCs of the present invention preferably have a crystallinity index (CRI) that is at least 3% greater than the CRI of the starting chitinous material. Advantageously, the CRI may be at least 5% greater than the CRI of the starting chitinous material. The CRI may be, for example, 89% or greater, or 90% or greater. The CRI may be in a range of 89-95%, or 90-95%.

The degree of deacetylation for chitin and the ChNCs is similar, indicating that the hydrolysis of chitin by persulfate does not lead to deacetylation of the amide groups, which is somewhat surprising. Deacetylation ChNCs may be subsequently effected to produce deacetylated ChNCs if desired. Deacetylation may be accomplished, for example, by the action of a base (e.g. a hydroxide such as NaOH or KOH), preferably at an elevated temperature (e.g. 60-100° C.), preferably in a solvent (e.g. water). The degree of deacetylation may be 15% or more, preferably in a range of 15-65%.

The present process is advantageously a one-spot process for producing ChNCs from biomass that has significant benefits in terms of scalability, safety, sustainability and low-cost. The stability and economic viability of persulfate renders it a suitable replacement for acids as strong oxidants. The present facile process provides a commercially viable method of obtaining ChNCs with enhanced uniformity and crystallinity and with smaller diameters and larger aspect ratios. Further, ChNCs produced in the present process are surface carboxylated, which renders them more reactive and improves their flexibility and processability in composites. In contrast, other acid hydrolysis procedures produce ChNCs having no surface carboxylate groups. Together with amino and acetamide groups in the chitin structure, the presence of carboxylic groups in ChNC could be the basis for many additional substitution reactions that make chitin more promising than cellulose as a candidate for functionalized materials from nature. The excellent intrinsic properties of ChNCs such as high tensile strength, biocompatibility, non-toxicity, renewability, and biodegradability, open diversified applications in a wide variety of areas, e.g., medicinal and pharmaceutical applications, cosmetics, the treatment of industrial pollutants, food, textiles, plastic reinforcement and aerogels.

Further features will be described or will become apparent in the course of the following detailed description. It should be understood that each feature described herein may be utilized in any combination with any one or more of the other described features, and that each feature does not necessarily rely on the presence of another feature except where evident to one of skill in the art.

BRIEF DESCRIPTION OF THE DRAWINGS

For clearer understanding, preferred embodiments will now be described in detail by way of example, with reference to the accompanying drawings, in which.

DETAILED DESCRIPTION

Figure 1:
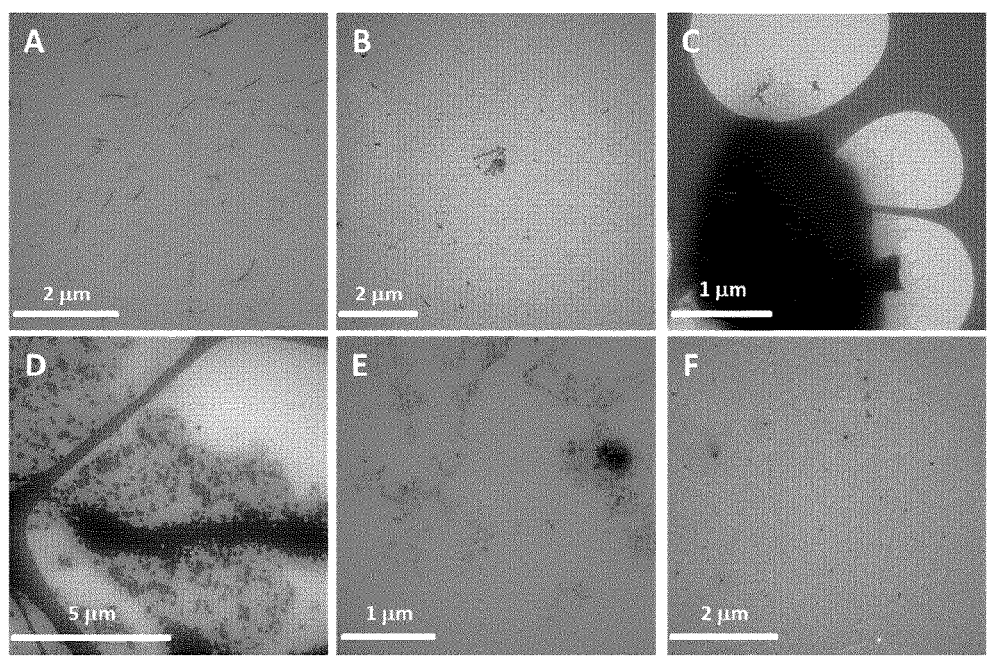
FIG. 1 depicts transmission electron microscope (TEM) images of (a) chitin, (b) dextran, (c) pullulan, (d) starch, (e) xanthan gum and (f) xylan treated with 1 M ammonium persulfate (APS) for 16 hours.

A versatile method using persulfate for the preparation of cellulose nanocrystals (CNC) is known in the art (Leung 2011; Leung 2012; Lam 2013). However, cellulose and chitin are two different compounds. The use of persulfate to break down other polysaccharides (e.g. chitin, xylan, dextran, pullulan, starch and xanthan gum) to form nanocrystals of the polysaccharides is not a priori expected in view of the process with cellulose because each polysaccharide has unique structural and bulk physical features that may disrupt nanocrystalline formation. For example, like amino acids and unlike cellulose, chitin is negatively charged in basic conditions due to carboxyl groups and positively charged in acidic conditions due to amino groups. Further, pristine chitin exhibits very high crystallinity compared to cellulose. Although the main bond is 1-4-β in both cellulose and chitin, the presence of N-acetyl groups of chitin can affect the hydrolysis as well as oxidation. The N-acetyl group may be oxidized or converted to other functional groups during the course of the APS treatment. To date, there are only a few reports for the production of chitin nanocrystals using acid hydrolysis (Fan 2008), which required the use of expensive chemicals. Indeed, as is shown in the Examples below, the only two polysaccharides tested that form nanocrystals from persulfate treatment are cellulose and chitin. Treatment of the other polysaccharides result in nanosized spheres, not a crystalline material.

EXAMPLES

Materials and Methods:

Ammonium persulfate (APS) and chitin practical-grade powder (C7170, $(C_8H_{13}NO_5)_n$ from shrimp shells) were obtained from Sigma Aldrich.

Attenuated total reflectance FTIR (ATR-FTIR) spectra were collected (Bruker Tensor 27 FTIR spectrophotometer) from 4000 to 600 $cm^{-1}$ for 64 scans and 4 $cm^{-1}$ resolution using a zinc selenide (ZnSe) crystal. Atomic force microscopy (AFM) micrographs of ChNCs were obtained from sonicated aqueous samples using a Nanoscope™ IV (Digital Instruments, Veeco, Santa Barbara, Calif.) with a silicon tip operated in tapping mode.

Low voltage transmission electron microscopy (LVTEM) micrographs were obtained by a Delong LVEM, low voltage electron microscope (Delong, Montreal, QC, Canada) operating in TEM mode at 5 kV. A ChNC suspension (10 mL) was prepared in double-distilled water at 0.1 wt % by sonication (3 min, app. 1 kJ). A 4 μL drop of the well-dispersed ChNC suspension was dried on a 300 mesh, Cu-300HD grid (Pacific Grid-Tech) and analyzed.

Wide angle X-ray scattering analysis was obtained on a Bruker Discover 8 diffractometer equipped with a copper (Cu Kα, λ=1.54184 Å) anode source, along with instrumental settings of 40 kV and 40 mA. The collected data were analyzed using WinPLOTR (http://www.llb.cea.fr/fullweb/winplotr/winplotr.htm), a graphic tool for powder diffraction to provide peak position (2 θ), FWHM (full width half maximum), peak deconvolution, and integration intensity for calculation of the crystallinity index (CRI). Crystallite sizes were calculated using the Scherrer equation $D=K\lambda/(FWHM \times \cos\theta)$ with the Scherrer constant K taken as 1 and λ=1.542 Å.

Thermogravimetric analysis (TGA) was conducted with a Netzsch STA 449F1 under nitrogen purge gas. Scanning electron microscopic (SEM) images were obtained using a Hitachi SEM (S-2600N, Tokyo, Japan) coupled with an energy dispersive X-ray (EDX) spectrometer equipped with a $LN_2$-free analytical silicon drift detector (INCA x-act, Oxford Instruments, UK). The SEM/EDX system was operated with a high vacuum mode at 20 kV, emission current of 80 μA, a working distance of 20 mm, and sample tilt of 30°. The EDX system has INCA software with a database of reference spectra for elemental analysis, compositional nano-analysis and mapping. Materials were immobilized on carbon tape and introduced into the chamber. To insure reproducibility, three different magnifications at three different areas were selected for each sample and data were averaged.

Dynamic light scattering and the ζ-potential of the ChNC materials (2 mg/mL) in water were determined using a Zetasizer Nano-ZS (Malvern Instruments, Malvern, UK) in triplicate. The NMR experiments were performed on a Bruker Avance spectrometer operating at a $^{13}C$ frequency of 150.9 MHz, using proton dipolar decoupling (tppm scheme with rf field of 80 kHz), magic angle spinning and cross-polarization. The rf field strength of 55 kHz for $^{13}C$ and a ramp from 80 to 40 kHz for $^1H$ were used for cross-polarization. The spin rate: 14 kHz, contact time: 2 ms, acquisition time: 13.7 ms, and recycle delay: 5 s.

Example 1

Preparation of Chitosan Nanocrystals (ChNCs) and Comparison to Other Polysaccharides Chitin (10 g) was added to a 1 M APS aqueous solution (1 L, pH 2, conductivity about 230 µS·cm$^{-1}$). The suspension was heated to 60° C. for 12 h to give a white suspension of ChNCs. The suspension was centrifuged (12,000 rpm, RCF=22,100) for 10 min. The solution was decanted, and about 200 mL of water was added to the ChNC pellet, followed by 5 min of vigorous mixing and repeated centrifugation. The centrifugation/washing cycles were repeated 4 times until the solution conductivity was about 5 µS·cm$^{-1}$ (pH about 4), close to that of deionized water. The product was lyophilized to yield a white powder (4.00 g). ChNCs in their sodium form were prepared by adding 1 M NaOH until the suspension reached pH 7, followed by washing/centrifugation with deionized water. During the APS treatment of chitin, selective oxidation occurs at the C6 primary hydroxyl group of chitin to form carboxylic acid groups (Scheme 1). Analogous to previous reports of CNC synthesis (Leung 2011; Leung 2012), the formation of ChNCs occurs via cleavage of the glycosidic bonds and individualization of elementary fibrils by the formation of charged carboxylate groups on surfaces of the chitin crystallites.

The resulting ChNCs could be subjected to a second treatment with NaOH for deacetylation to form ChNCs with improved aqueous solubility as follows. The deacetylation of ChNCs was performed using a modified procedure (Zhang 2005). ChNCs (1 g) were added to a 45% NaOH solution (4.5 g NaOH in 10 mL of water). The suspension was heated at 80° C. for 4 hours at which time the reaction mixture turned from white to brown. The brown suspension was washed with EtOH, centrifuged six times at 10,000 rpm for 10 min, and oven dried at 60° C. to yield a yellow-colored product (700 mg).

Figure 2:
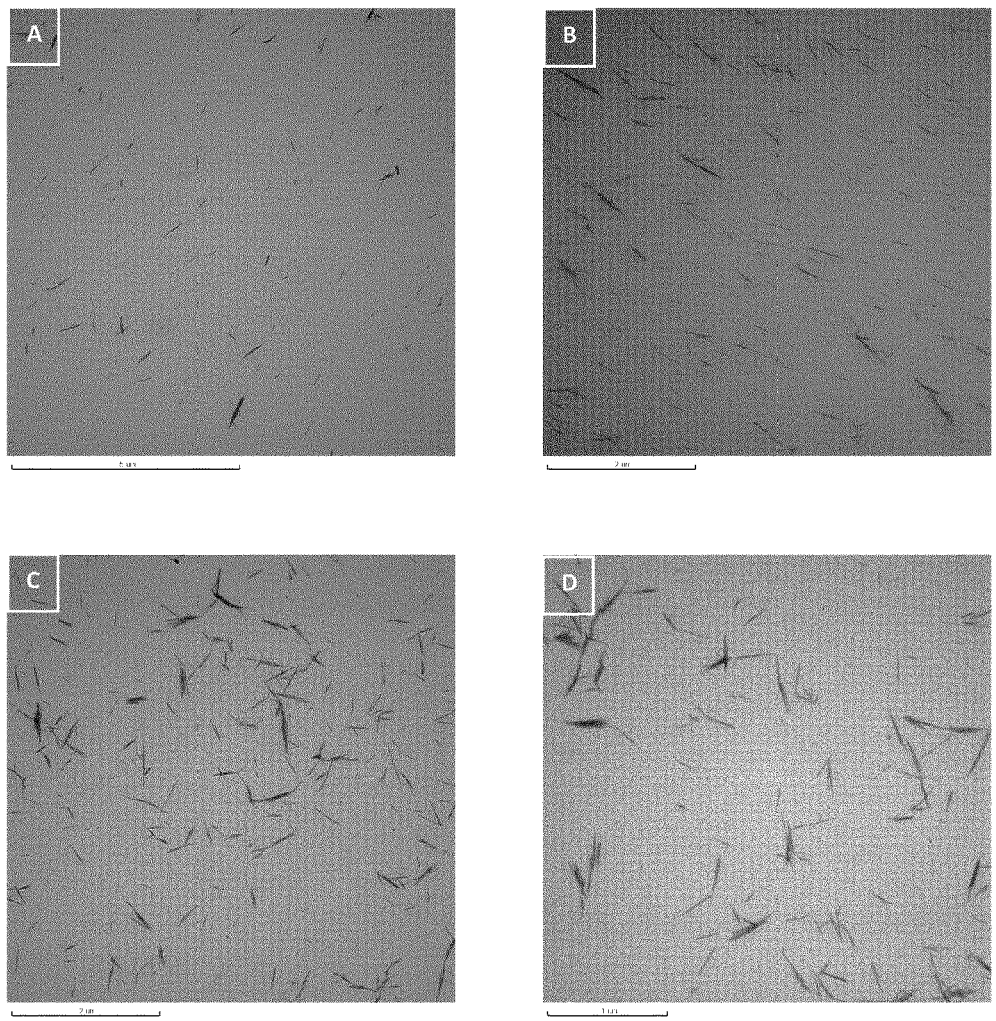
FIG. 2 depicts low voltage transmission electron microscopy (LVTEM) micrographs of chitin nanocrystals (ChNCs): A (×31 000), B and C (×50 000), and D (×81 000).

To evaluate whether other polysaccharide-based nanoparticles could be produced using APS, chitin, dextran (α-1,6 glycosidic linkages between glucose molecules, while branches begin from α-1,3 linkages), pullulan (three glucose units in maltotriose are connected by an α-1,4 glycosidic bond, whereas consecutive maltotriose units are connected to each other by an α-1,6 glycosidic bond), starch (amylose, α-1,4-D-glucopyranosyl and α-1,6-glucopyranosyl), xanthan gum, and xylan (a polymer of β-D-xylose, a pentose sugar) were treated with 1 M APS at 60° C. for 16 h. The reaction products were dialyzed and evaluated with TEM for their dimension as shown in FIG. 1. Considering the backbone similarity between xanthan and cellulose, the hydrolysis of 1,4-β bonds by APS was greatly dependent upon the polymer structure. It should be noted that xanthan has a particularly complicated molecular structure with the backbone β-(1-4)-D-glucose, same as cellulose. However, every alternate glucose residue has a three sugar side chain comprising two mannose residues with a glucuronic acid residue between them. The mannose residue nearest the main chain can carry a C6 acetyl group and the terminal mannose can carry a pyruvate group between C4 and C6. No nanorods were observed from xylan, a pentose sugar with 1-4-β bonds, attesting that the action of APS was only limited to chitin or cellulose, and not for other polysaccharides. Indeed, the reaction of other polysaccharides with APS only yielded spherical nanoparticles whereas only the reaction of chitin with APS yielded individual rod-shape nanoparticles (FIG. 2).

Example 2

Characterization of Chitosan Nanocrystals (ChNCs)

Figure 3:
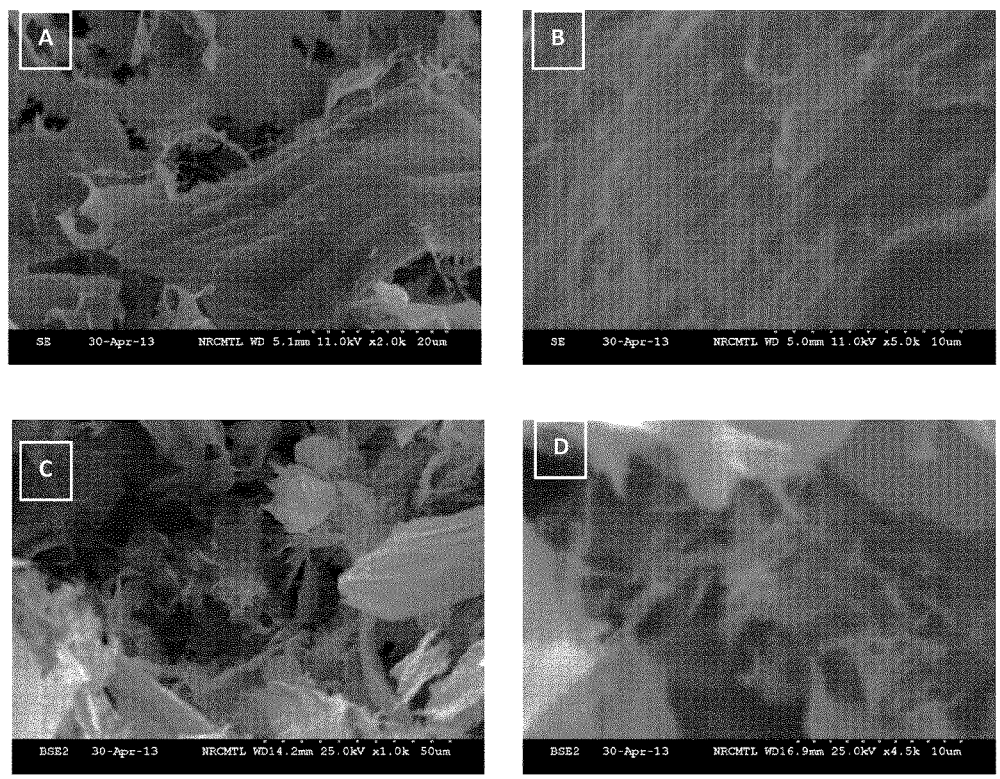
FIG. 3 depicts scanning electron microscope (SEM) micrographs of freeze-dried chitin nanocrystals (ChNCs) bundles prior to dispersion in water. Both detectors, SE (A, B) and BSE (C, D) were applied in order to perceive the fibrous structure of the material prior its dispersion in water.
Figure 4:
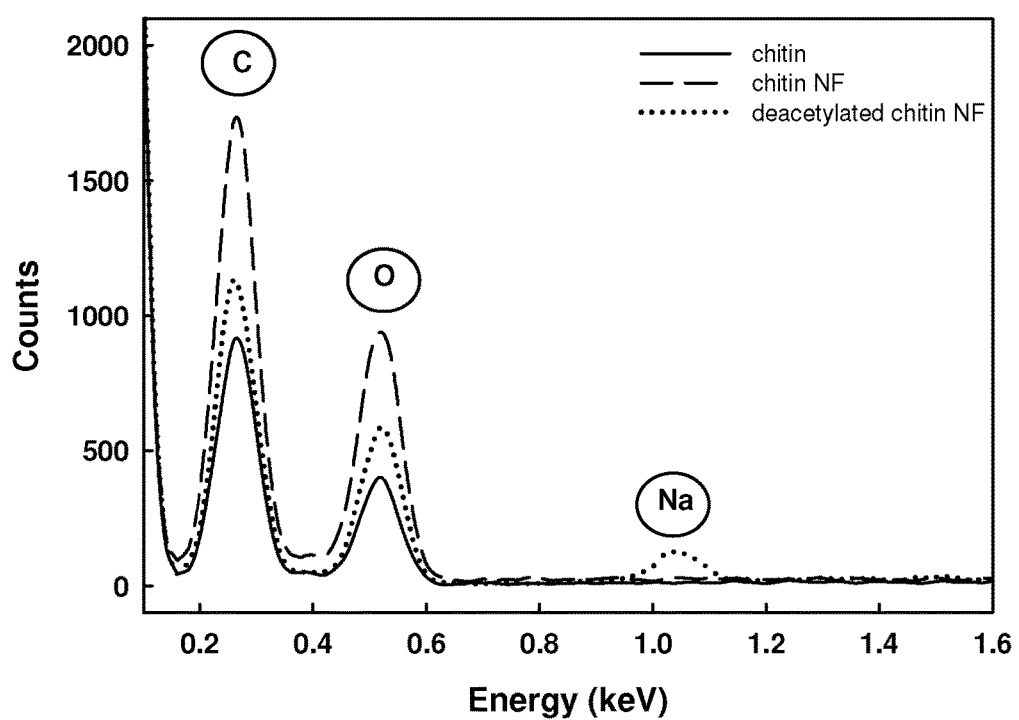
FIG. 4 depicts representative energy dispersive X-ray (EDX) spectra of chitin, chitin nanocrystals (ChNCs) and deacetylated chitin nanocrystals (deacylated ChNCs) after 4 h treatment in NaOH.
Figure 5:
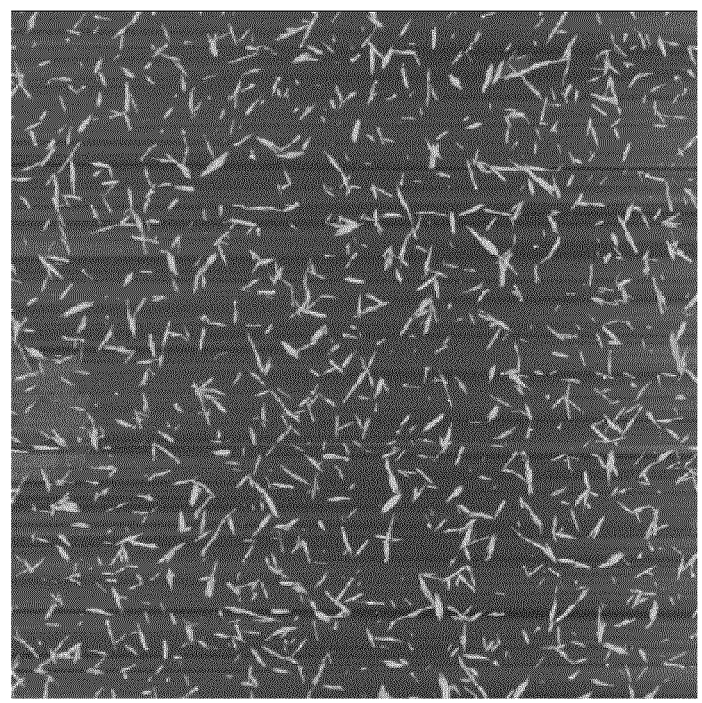
FIG. 5 depicts an atomic force microscope (AFM) micrograph (10 μm×10 pm) showing chitin nanocrystals (ChNCs) produced using ammonium persulfate (APS) treatment.

SEM images of the ChNCs prepared in Example 1 revealed a perceived fibrous structure prior to its dispersion in water (FIG. 3). EDX spectra of various forms of chitin and their elemental analyses are presented in FIG. 4 and Table 1, respectively. Upon treatment of chitin with APS, an increase in oxygen content was consistent with the oxidation of the C6 alcohol group to the carboxylic group. Deacetylation of ChNCs with NaOH results in a decrease in the oxygen content as the acetyl groups of chitin were converted to amino groups. The dimensions and size distributions of ChNCs were estimated using AFM. For a sample of 1069 ChNCs in the AFM image, the average length and width were (149±7) nm and (6.8±0.1) nm, respectively (FIG. 5). Dynamic light scattering of ChNCs (2 mg/mL solution in water) estimated a size distribution of 112 ±1 nm and a ζ-potential of −42 mV. The high ζ-potential (negative or positive above 40 mV) conferred the stability of a colloid dispersion (Lam 2013), which is important for numerous potential applications such as coating, polymer fillers and drug delivery.

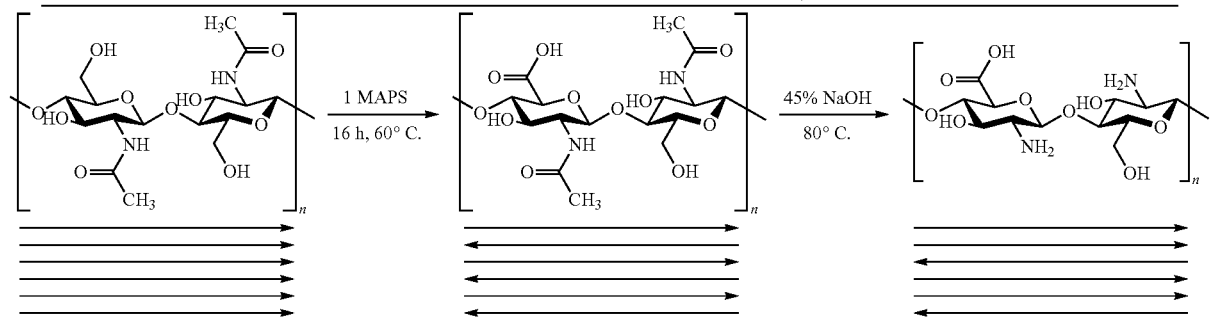

Scheme 1. (Upper) Selective oxidation occurs at the C6 primary hydroxyl group during the APS treatment. In a second step, ChNCs can be treated with NaOH for deacetylation. (Lower) Molecular arrangement of β-chitin, α-chitin and γ-chitin (left, middle and right).

TABLE 1

Elemental Analysis of Various Forms of Chitin

| Element | Chitin Weight % | Chitin Atomic % | ChNC Weight % | ChNC Atomic % | Deacylated ChNC after 4 h treatment Weight % | Deacylated ChNC after 4 h treatment Atomic % |
|---|---|---|---|---|---|---|
| C (K) | 55.68 | 62.59 | 42.69 | 56.81 | 52.69 | 60.05 |
| O (K) | 44.31 | 37.41 | 50.31 | 43.18 | 45.28 | 38.74 |
| Na (K) | — | — | — | — | 2.02 | 1.21 |

Figure 6:
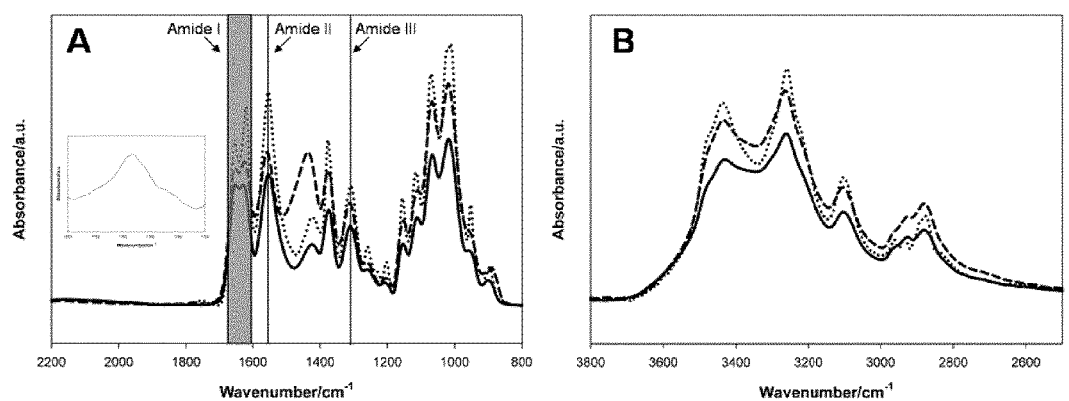
FIG. 6 depicts (A) FTIR spectra from 2200 to 800 $cm^{-1}$ and (B) FTIR spectra from 3800 to 2500 $cm^{-1}$ for chitin (black line), chitin nanocrystals (ChNCs) (red line), deacetylated chitin nanocrystals (deacylated ChNCs) after 4 h in NaOH (green line). Inset of A: COON band centered at 1753 $cm^{-1}$ for ChNCs.

FTIR spectra of the different chitin materials are shown in FIG. 6 with peak assignments given in Table 2. All three species exhibit distinct amide I doublet bands centered at 1620 and 1655 cm$^{-1}$, amide II band at 1554 cm$^{-1}$ and amide III band at 1305 cm$^{-1}$. For the amide I, about 50% carbonyl groups are bonded through hydrogen bonds to the amino group inside the same chain (C=O ... H—N) as reflected by the vibration mode at 1655 cm$^{-1}$. The remaining groups produce the same bond plus another with the —CH$_2$OH group from the side chain, resulting in a decrease in the amide I band at 1620 cm$^{-1}$. The amide II is attributed to N-H bending vibration (40-60%) and from the C—N stretching vibration (18-40%). The amide III is a very complex band resulting from a mixture of several coordinate displacements (FIG. 6A). These amide bands are consistent with the α-polymorphic crystalline structure of chitin (Jang 2004). The amide I peaks of ChNCs are more pronounced than the starting chitin, particularly the peak at 1620 cm$^{-1}$. The inset of FIG. 6A also shows a distinct ν(C=O) stretching peak at 1753 cm$^{-1}$ for the COON group of ChNCs.

The deacetylation of ChNCs results in several changes to the amide I bands. Neutralization of the COON group in deacetylated ChNCs should shift the resulting COO$^{31}$ Na$^+$ peak downfield leading to an absorbance increase centered at 1654 cm$^{-1}$ (Lam 2013). However, the loss of acetyl groups will lower both the absorbance bands at 1654 and 1621 cm$^{-1}$ as a result of decreasing amide character. The net result is a reduction in the relative ratio between the two doublet amide I peaks for deacetylated ChNCs in comparison to ChNCs. FIG. 6B shows the amide A band at 3262 cm$^{-1}$ for intermolecular C=O ... H—N hydrogen bond and the amide B band at 3103 cm$^{-1}$ for NH groups intramolecularly bonded by H. Again, the vibrational bands decrease in absorbance, particularly for the amide A band of deacetylated ChNCs as acetyl groups are replaced by NH$_2$ groups, reducing the number of intermolecular C=O ... H—N hydrogen bonds in the system. The increase in absorbance band for the OH groups at 3437 cm$^{-1}$ could be attributed to the presence of water in addition to the hydroxyl and carboxyl group of the chitin material.

TABLE 2

FTIR Spectra Peak Assignment of the Chitin Material

| | Chitin (cm$^{-1}$) | ChNCs (cm$^{-1}$) | Deacetylated ChNCs (cm$^{-1}$) |
|---|---|---|---|
| OH | 3429 | 3437 | 3439 |
| Amide A (asNH) | 3261 | 3260 | 3264 |
| Amide B (sNH) | 3102 | 3103 | 3108 |
| asCH$_3$ | 2960 | 2962 | 2960 |
| sCH$_2$ | 2929 | 2934 | 2928 |
| CH$_3$ | 2877 | 2877 | 2876 |
| COOH | — | 1753 | — |
| Amide I (C=O) | 1654 | 1655 | 1656 |
| Amide I (C=O) | 1622 | 1620 | 1621 |
| Amide II (CN and NH) | 1554 | 1554 | 1557 |
| CH$_2$ | 1428 | 1417 | 1429 |
| CH and C—CH$_3$ | 1376 | 1376 | 1377 |
| Amide III (CN and NH) | 1308 | 1308 | 1310 |
| NH | 1260 | 1258 | 1259 |
| C—O—C | 1155 | 1155 | 1155 |
| C—O | 1113 | 1115 | 1115 |
| C—O | 1069 | 1071 | 1072 |
| C—O | 1025 | 1012 | 1024 |
| CH$_3$ | 952 | 952 | 953 |
| CH | 896 | 896 | 896 |
| Amide V (NH) | 703 | 702 | 703 |

It should be noted that the FTIR spectra of ChNCs could be used to estimate the carboxylic acid and N-acetylation contents. The absorption ratio $A_{1740}/A_{1030}$ between the carboxylic acid stretching band (1740 cm$^{-1}$) and the C-O stretching band of the chitin backbone (1030 cm$^{-1}$) can be used to estimate the carboxylic acid content of cellulose (Habibi 2006). The $A_{1740}/A_{1030}$ estimated a carboxylic acid content of 0.058 with ChNCs, in agreement with the result obtained by conductometric titration as described below.

Figure 7:
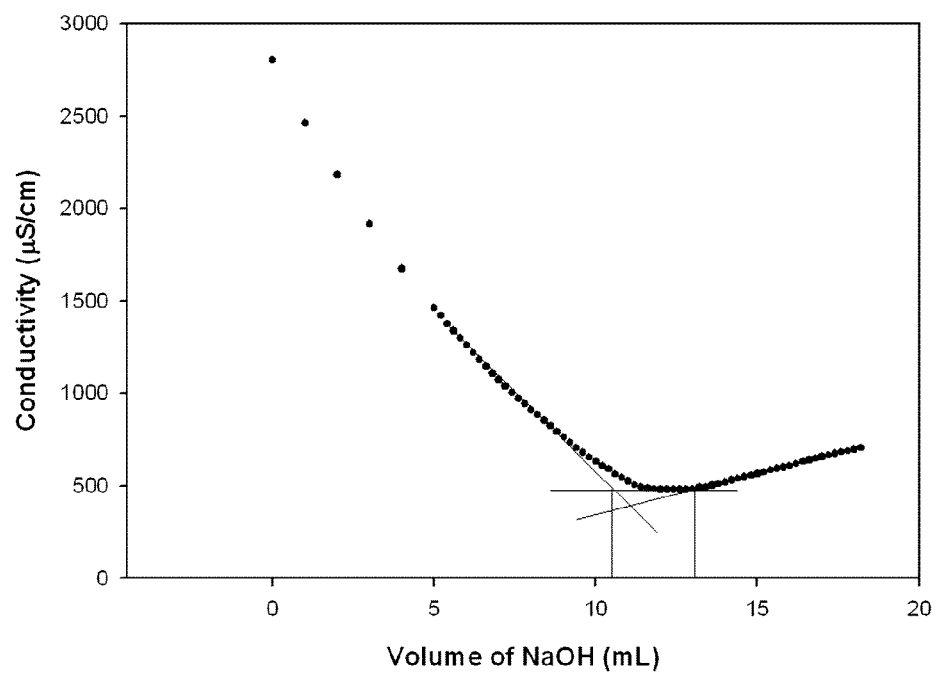
FIG. 7 depicts a conductometric titration of chitin nanocrystals (ChNCs) (DO=0.06).

Conductometric titration was conducted using a known method for carboxylated cellulose nanocrystals (Leung 2011) to determine the carboxylic acid content or the degree of oxidation (DO) of the ChNCs. ChNCs (50 mg) were suspended in 10 mL of 0.01 M HCl and sonicated for 10 min to disperse the nanocrystals. The ChNC suspension was then titrated against 0.01 M NaOH and DO is calculated as $203(v_2-v_1)C/(w-14(v_2-v_1)C)$, where C is the NaOH concentration (M), w is the weight of ChNC sample (g), and $v_1$ and $v_2$ are the volumes of NaOH (L). The molecular weight of an N-acetylglucosamine unit with a CH$_2$OH group is 203. The molecular weight difference between an N-acetylglucosamine unit and its COON derivative is 14. The titration was repeated three times. FIG. 7 shows the titration plot. Three segments can be observed in the conductometric titration plot. The first descending segment is the neutralization of excess HCl used in protonating the ChNCs. The second flat segment corresponds to the neutralization of carboxyl groups and the third ascending segment refers to the excess NaOH. A DO value of $(6.2\pm0.8)\times10^{-2}$ was obtained by conductometric titration, which agreed well with the FTIR estimation using the $A_{1740}/A_{1030}$ ratio as mentioned earlier.

The degree of deacetylation (DD) was determined by FTIR with the results presented in Table 3. The corrected baseline FTIR absorbance intensity ratio (Fan 2008) between the bands at 1560 and 1030 cm$^{-1}$ was obtained using the regression equation (Shigemasa 1996):

$$I_{1560}/I_{1030}=-0.00714(DD)+0.796$$

The DD values for chitin and ChNCs by FTIR are similar, which confirmed that oxidation of chitin by APS did not lead to deacetylation of the amide groups. An alternative method (Baxter 1992) has been commonly used for determining the degree of N-acetylation which takes into account the transmission bands at 3450 and 1655 cm$^{-1}$ as % N-acetylation=$115\times(I_{1650}/I_{3450})$. However, the values for N-acetylation are only applicable for chitosan materials in the range of 0-55%. As previously mentioned, the band at 3450 cm$^{-1}$ is attributed to OH and might include contributions from absorbed water. Also, the amide I band at 1650 cm$^{-1}$ typically appears as a doublet in both α-chitin and highly acetylated materials. This leads to very subjective baseline corrections required for band intensity measurements (Shigemasa 1996).

TABLE 3

Comparison of Degree of Deacylation (DD) of Various Chitin Species

| Sample | Degree of Deacylation (DD) % |
|---|---|
| Chitin | 9.6 |
| ChNCs | 9.0 |
| Deacylated ChNCs 1 h | 39.3 |
| Deacylated ChNCs 2 h | 41.6 |
| Deacylated ChNCs 4 h | 55.2 |
| Deacylated ChNCs 8 h | 59.2 |
| Deacylated ChNCs 16 h | 63.4 |
| Chitosan | 85.8 |

Figure 8:
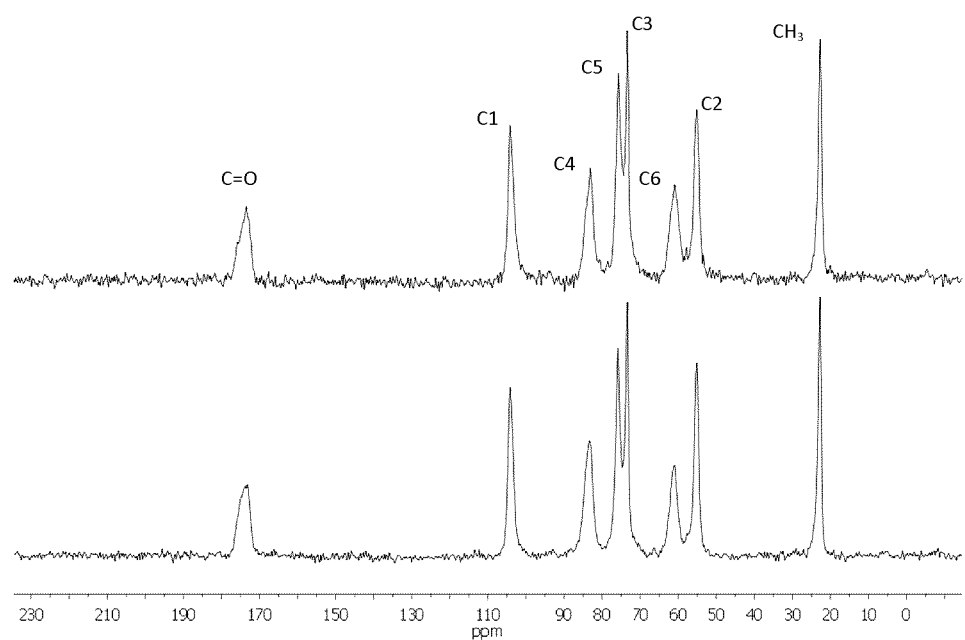
FIG. 8 depicts $^{13}C$ NMR spectra of chitin (top) and chitin nanocrystals (ChNCs) (bottom). DA is estimated as $6*I_{CH3}/(I_{C1}+I_{C2}+I_{C3}+I_{C4}+I_{C6}+I_{C6})$ where I is the peak area.

FIG. 8 compares the $^{13}$C CP-MAS spectra for ChNCs and the chitin starting material. The C3 and C5 appear as two signal characteristics of a partially solved doublet, a typical signature of α-chitin. The doublet has been attributed to the different configurations of C3 and C5 resulting from the hydrogen bonds formed. The DD was then estimated by comparing the carbon signals of the methyl and polysaccharide backbone (Cardenas 2004). The DD was calculated to be 2% for both the chitin and ChNC, confirming that the APS treatment did not result in deacetylation of the amide groups.

Figure 9:
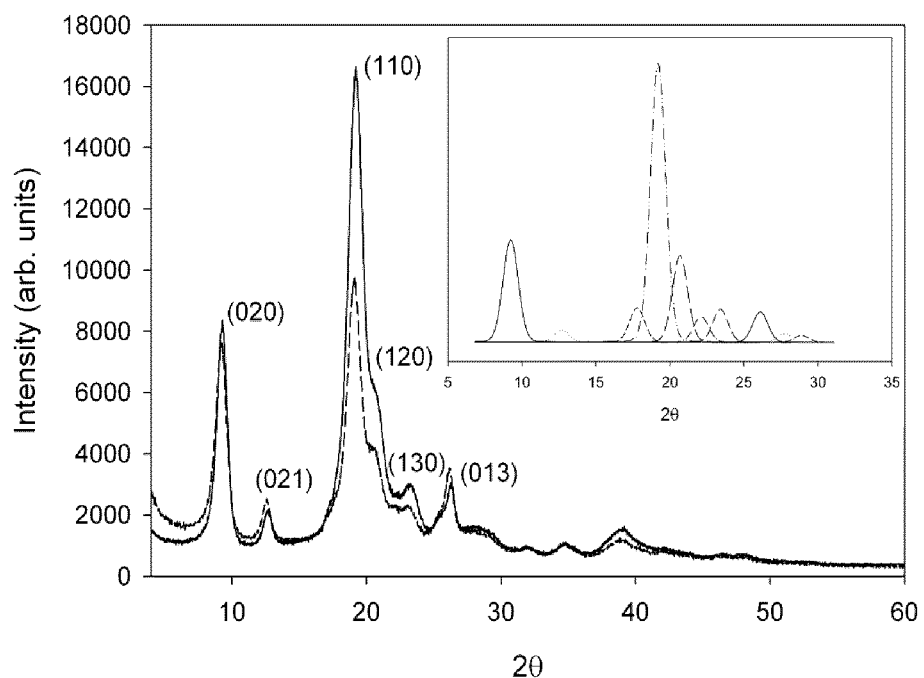
FIG. 9 depicts X-ray diffraction (XRD) spectra of chitin (dotted line) and chitin nanocrystals (ChNCs) (solid line) and peak deconvolution of the ChNC spectrum (inset). The crystallinity index (CRI) is estimated as $(I_{110}-I_{am})/I_{110}$ where $I_{110}$ the intensity area of the 110 peak, $I_{am}$ is the intensity area of the amorphous peak (at)16°.
Figure 10:
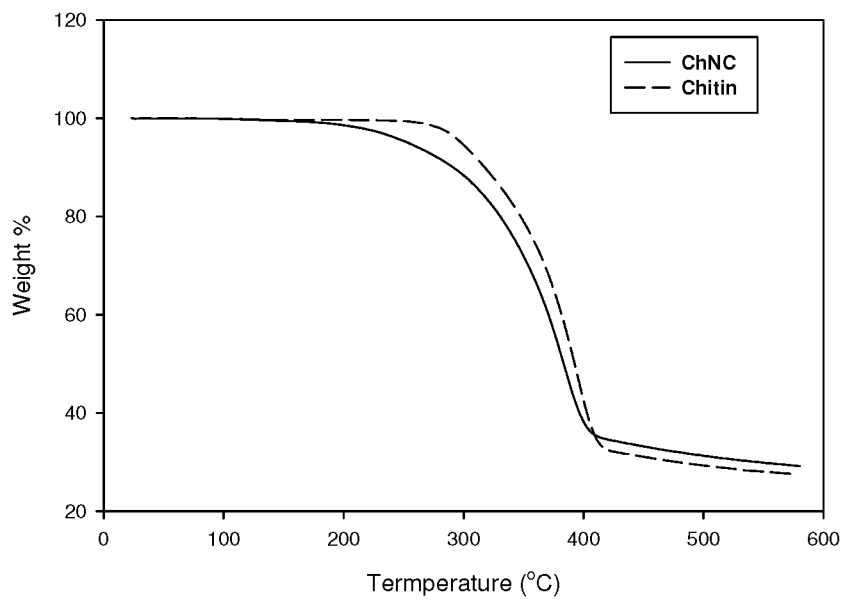
FIG. 10 depicts thermogravimetric analysis (TGA) of chitin starting material and chitin nanocrystals (ChNCs) showing a decrease in thermostability after ammonium persulfate (APS) treatment.

The crystal structures of ChNCs were studied using XRD. As shown in FIG. 9, ChNCs exhibit four diffraction peaks at 9.6°, 19.6°, 21.1° and 23.7°, a pattern that resembles the diffraction pattern of α-chitin. After treatment with APS, the intensity of the (110) diffraction peak increased significantly, indicative of an increase of crystallinity. Using the intensity method reported by Lavall et al. (Lavall 2007), the crystallinity index (CRI) of the ChNCs was estimated to be 91.7%, an increase from 86.5% of α-chitin. Such a result was compared favorably with the literature values of 86% for chitin nanowhiskers (Heath 2013). It should be noted that the oxidation of chitin led to a decrease in the thermal degradation temperatures, $T_{d5}$ decrease from 298° C. for the chitin starting materials to 253° C. for ChNCs (FIG. 10).

Aqueous solubility of ChNCs and chitin was examined. Samples of chitin, acid form ChNCs and neutralized ChNCs were dissolved in water at 1% (100 mg/10 mL), with resulting pHs of 5.0, 3.5 and 6.0, respectively. Chitin was insoluble and settled to the bottom of the vial. The acid form of ChNCs was slightly soluble, but also settled to the bottom of the vial within 10-20 min. In contrast, neutralized ChNCs formed an opaque solution with very little sedimentation. All samples were then sonicated (1000 J, i.e. 10 kJ/g) on ice and left to settle for 20 min. Chitin was still insoluble and sedimented. The acid form of ChNCs formed an opaque solution which did not sediment, whereas the neutralized ChNC became more translucent (less opaque) compared to the non-sonicated counterpart. Increasing the sonication energy to 20 kJ/g had a marginal impact on the solubility.

Example 3

ChNC Plausible Cytotoxicity

Electric cell-substrate impedance sensing (ECIS) was performed using *Spodoptera frugiperda* Sf9 insect cells and V79 Chinese hamster lung fibroblast cells. These two cell lines have been used extensively for ECIS testing and the culture conditions have been previously described (Male 2012). The ECIS impedance system (Applied Biophysics, Troy, N.Y.) comprises an 8-well sensing chip (8W1 E) with a gold electrode in each well. Detailed information on ECIS impedance measurement using microfabricated gold electrodes (250 pm) has been reported elsewhere (Male 2012). Cell adhesion was promoted by the addition of an extracellular matrix (ECM) to the gold surface as previously described. Fibronectin (0.15 mL, 0.1 mg/mL, prepared in 0.85% NaCl) and concanavalin A (Con A, 0.40 mL, 0.5 mg/mL, prepared fresh daily in 50 mM PBS, pH 7.4 with the aid of sonication for 1 h) were used for V79 and insect cells, respectively.

After about 60 min of incubation, the wells were washed three times with 0.85% NaCl and then 0.3 mL of culture medium was placed in each well, and the impedance baseline was monitored for 1-2 hours at 37° C. in a humidified chamber of 5% $CO_2$ and 95% air (V79 cells) or at 27° C. without $CO_2$ for insect cells. The wells were then emptied before the addition of the cell-ChNC solution. A ChNC sample (stock solutions in the range of 2000 ppm in culture medium) was added (25-500 μL) to the V79 cell suspension (0.5 mL at 2×10$^6$ cells/mL) resulting in various concentrations (50-1000 ppm) once the sample was made up to 1 mL with culture medium. In the case of insect cells, the ChNC sample was added (12.5-75 μL) to the cell suspension (0.5 mL at 6×10$^6$ cells/mL) resulting in various concentrations (25-150 ppm) once the sample was made up to 1 mL with culture medium having a final ethanol concentration of 2%. For testing cytotoxic/inhibitory effects, 0.4 mL of each sample concentration was added to 2 or 3 wells. Six concentrations of ChNCs including a control (no ChNCs) were tested at the same time and each experiment was performed in triplicate. After the experiment, cells were imaged using a Wilovert AFL 30 inverted microscope (Hund, Germany) equipped with a digital video camera (KP-D50U, Hitachi, Tokyo, Japan).

The impedance/resistance of each well was measured every 2 min for 20 hours at 4 kHz, and the system acquires resistance, impedance and capacitance data. However, focus for study was placed on the larger changes in the resistance. The ECIS$_{50}$ value derived from the time response function, f(C, t), was calculated as previously described (Male 2012).

Figure 11:
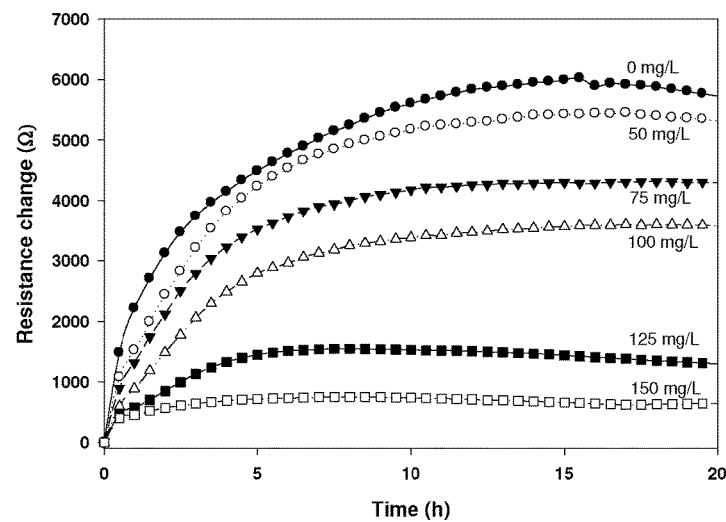
FIG. 11 depicts resistance response of Sf9 insect cells to varying concentrations of chitin nanocrystals (ChNCs).

Without ChNCs, the V79 cells descended to the well bottom within 20 min and changed their morphology from round shapes to flattened forms with much larger dimensions as observed by the video-enhanced microscope. Low concentrations (<250 ppm) of ChNCs exhibited a very slight effect on the resistance signal. At higher concentrations (500-1000 ppm), the resistance change was lower by 20%, but the cells on the electrode surface were still well spread. This phenomenon was likely due to cells initially trying to spread flat on the electrode surface, but then becoming more spherical on the surface with time due to the influence of ChNCs. Similarly, without ChNCs, the Sf9 cells descended to the well bottom within 20 min and changed their morphology from round shapes to flattened forms with much larger dimensions as observed by the video-enhanced microscope. As the cells spread, the effective area available for current flow was altered, resulting in a significant increase in the resistance of the well by about 6.0 kΩ to a final resistance of 9.0 kΩ. Low concentrations of ChNC samples (<50 ppm) exhibited a marginal effect on the resistance signal with insect cells. However, as the concentration was increased (75-150 ppm), the resistance change decreased significantly (FIG. 11). Inverted fluorescent microscopy confirmed that the insect cells in the absence of ChNCs were intact and well spread on the Con A-coated electrode surface even after washing the wells with saline three times. However, insect cells exposed to ChNCs (>100 ppm) for 24 h were spherical compared to the control cells. The ChNC effect was more of an inhibitory effect at the cell-substratum binding level rather than a cytotoxic effect as dead cells were not observed. An $ECIS_{50}$ value of 123 ±16 ppm was calculated for ChNCs. Thus, ChNCs are virtually non-cytotoxic.

Cell counting by the Trypan Blue exclusion assay performed at 0, 4.5, 8, and 24 hours indicated that cell viability was still above 95% when insect cells were exposed to 50-400 ppm ChNCs. The pattern observed correlated well with the ECIS where cytotoxic effects were not observed. There was also negligible effect of the ChNC sample (50 and 200 ppm) on the cell growth (doubling time from 2.96 x $10^6$ to 4.88 x $10^6$ cells/mL over about 24 hours as expected from the control) over the experiment course as the cell densities were similar after 24 hours. However, at the highest concentration (400 ppm) of ChNCs, a small effect on the cell growth was noted after 24 hours with a drop of 25% (3.75×$10^6$ cells/mL). Thus, at concentrations below 200 ppm, ChNC did not affect the viability Sf9 insect cells, indicating its virtual non-cytotoxicity.

Example 4

Adsorption Kinetics of Methylene Blue (MB)

The adsorption capacity of methylene blue (MB, MW about 320 g/mol, Sigma-Aldrich) on ChNCs is calculated as $q = V(C_o-C_t)/m$ where V is the solution volume, $C_o$ is the initial MB concentration, $C_t$ is the MB concentration in the solution at a given time (t), and m is the ChNC adsorbent mass (He 2013). All containers used for MB solutions were of polypropylene to minimize the dye adsorption. For each initial dye concentration ($C_o$), the amounts of MB adsorbed at a given time, $q_t$, can be related to $C_t$. Non-linear regression analysis was then applied to estimate the equilibrium values for $q_e=V(C_o-C_e)/m$, where $C_e$ is the equilibrium concentration of MB in solution A plot of $q_e$ vs. $C_e$, then performed to validate the applicability of the Langmuir isotherm equation, $q_e=q_{max} \cdot K_L C_e/(1+K_L C_e)$ where $q_{max}$ is the Langmuir constant related to maximum adsorption capacity and $K_L$ is the Langmuir constant related to binding energy of the adsorption system. The $q_{max}$ value was then used for the estimation of the specific surface area (SSA) of ChNC as $(q_{max}/MW) \times \alpha_{MB} \times N_{Avo}$ where MW is the molecular weight of MB, $a_{MB}$ is the occupied surface area of one MB molecule (about 1.3 $nm^2$, assuming the MB molecule is lying flat on the adsorbent surface, 17.0×7.6 =about 130 $Å^2$) and $N_{Avo}$ is the Avogadro number (6.023×$10^{23}$ $mol^{-1}$) (He 2013).

The plot of MB absorbance at 660 nm ($Abs_{660nm}$) vs. MB concentration [MB] was linear up to 20 μM with a slope of 0.062 $Abs_{660nm}$/μM [MB]. Aqueous solutions (12 mL) containing different concentrations of MB (100-1200 μM, diluted from a 4 mM stock solution in 20 mM phosphate buffer, pH 7.5), were added to samples (12 mg) of ChNCs and rotated. Small samples (about 300 μL) were taken every 30 s for the first 3 min and then at 4, 5, 10, 20, min. These samples were immediately centrifuged at 12,000 rpm and the supernatants (after centrifugation) were tested (diluted 10-100 times depending on the concentration of MB) for the residual concentration of MB left in solution, following any MB binding to the adsorbent, and compared to the starting concentration. The amount of MB bound (mg) was then calculated and the MB adsorption in mg/g of sample was determined. Unless otherwise indicated, the binding experiments were performed at ambient temperature, 22 ±1° C. and neutral pH.

Figure 12:
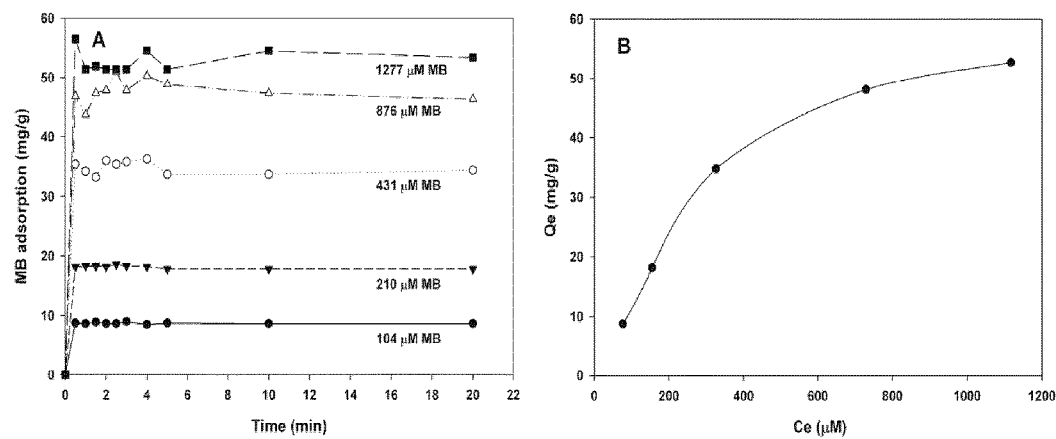
FIG. 12 depicts: (A) Adsorption kinetics at different concentrations (μM) of methylene blue (MB) on chitin nanocrystals (ChNCs); (B) Langmuir adsorption isotherm of MB on ChNCs.

The adsorption capacity of ChNCs increased rapidly and reached equilibrium within 2 min (FIG. 12A) with the adsorption data well represented by the pseudo-first-order model or pseudo-second-order model (Table 4). As shown in FIG. 12B, the Langmuir isotherm model (Langmuir 1918), $q_e=q_{max}K_L C_e/(1+K_L C_e)$, appeared to well represent the binding data for MB on ChNCs (correlation coefficient of $R^2$=0.987) with a maximum MB loading capacity ($q_{max}$) for ChNC of 75.32 mg/g (SE: standard error =6.59). Estimated kinetic parameters of the two adsorption isotherms for MB are given in Table 5. Accordingly, $C_e^*=1/K_L$ ($K_L$=0.0023 $μM^{-1}$; SE=0.0005), whereby the loading is 50% of the maximum capacity, was estimated to be 434.8 μM for ChNCs. The $q_{max}$ value for CNC prepared by the similar APS procedure was 101.2 mg/g (He 2013). Based on the $q_{max}$ estimated from the Langmuir model for ChNCs (Table 3), a specific surface area (SSA) of 184 $m^2$/g was estimated for ChNC compared to the theoretical value of 410 $m^2$/g. The latter was derived by considering ChNCs as a cylinder with a length of 149 nm, a diameter of 3.4 nm, and a density of 1.462 g/$cm^3$. SSA for 1 g of ChNCs is estimated as $N \cdot S_a$ where $S_a$ is the surface area of one ChNC molecule or 2 π$(radius)^2$ +2 π(radius)x(length). The number (N) of ChNC molecules per gram is estimated as $V_T/V_S$ where $V_s$ is the volume of one ChNC molecule or 2 π$(radius)^2$x(length) and $V_T$ is the volume for 1 g ChNC =1/density.

TABLE 4

| Pseudo-first-order and Pseudo-second-order Adsorption Kinetics | | |
|---|---|---|
| Pseudo-first-order kinetics | $\frac{dc}{dt} = -k_1 C$ or $C = C_o e^{-k_1 t}$ | (1) |
| | where $k_1$ ($min^{-1}$): the rate constant $q_t$: the amounts of dye adsorbed at a given time | |
| | $q_t = q_e (1 - e^{-k_1 t})$ | (2) |
| | where $q_e = V C_o/m$: the amounts of dye adsorbed at equilibrium $C_o$ = initial concentration of MB m = amount of the adsorbent V= volume of the MB solution | |
| Pseudo-second-order kinetics | $\frac{dC}{dt} = -k_1 C^2$ or $\frac{1}{c} - \frac{1}{c_o} = k_1 t$ | (3) |
| | $q_t = \frac{q_e c_o k_1 t}{1 + c_o k_1 t} = \frac{q_e^2 k_2 t}{1 + q_e k_2 t}$ | (4) |
| | where $k_2 = (m/V) k_1$ | |

TABLE 5

Estimated Kinetic Parameters of the Two Adsorption Isotherms MB

| ChNC | Equation | Parameter | MB concentration (µM) | | | | |
|---|---|---|---|---|---|---|---|
| | | | 104 | 210 | 431 | 876 | 1277 |
| Pseudo 1$^{st}$ order | $q_t = q_e(1 - e^{-k_1 t})$ | $q_e$ | 8.72 | 18.2 | 34.8 | 47.7 | 52.7 |
| | | R-square | 0.999 | 0.999 | 0.995 | 0.991 | 0.994 |
| Pseudo 2$^{nd}$ order | $q_e = (q_e^2 k_2 t)/(1 + q_e k_2 t)$ | $q_e$ | 8.73 | 18.1 | 34.8 | 48.4 | 52.8 |
| | | R-square | 0.99 | 0.999 | 0.995 | 0.992 | 0.994 |

Example 5

Optimization of ChNC Production

The production process described in Example 1 was optimized to reduce the amount of ammonium persulfate (APS) spent and to maximize the production yield of chitin nanocrystal (ChNC) per reaction. Specifically, the amount of chitin added to the reaction was increased from 1 wt % to 15 wt % (chitin:APS ratio from 1:22.8 to 1:1.5) and the resulting product was analyzed for yield, degree of oxidation (DO), and the distribution of nanocrystals (see Table 6). Reactions starting with 1 wt % to 5 wt % chitin resulted in similar yields and the ChNCs have similar degrees of oxidation (DO). TEM micrographs of these samples showed uniformly distributed nanocrystals with no significant differences in particle sizes between the samples. At 10 wt % chitin, nanocrystals were again observed with TEM, but the DO is significantly lower than the other samples. At 15 wt % chitin, TEM showed a wide distribution of particle sizes, with the majority being in the micron range. Therefore, 10 wt % chitin appears to be an optimal condition to produce ChNC in high yield while minimizing the amount of APS used in the reaction.

TABLE 6

Optimization of ChNC Production

| Chitin (wt %) | Chitin:APS Ratio (wt) | Yield (%) | Residual APS (M) (6 h) | Residual APS (M) (12 h) | DO by Titration (%) | TEM Observations |
|---|---|---|---|---|---|---|
| 1 | 1:22.8 | 53 | 0.47 | 0.28 | 7.31 | Nanocrystals |
| 2 | 1:11.4 | 59 | 0.43 | 0.26 | 8.26 | Nanocrystals |
| 3 | 1:7.6 | 41 | 0.12 | 0 | 8.05 | Nanocrystals |
| 4 | 1:5.7 | 40 | 0.18 | 0 | 8.04 | Nanocrystals |
| 5 | 1:4.6 | 38 | 0 | 0 | 7.99 | Nanocrystals |
| 10 | 1:2.3 | 58 | 0 | 0 | 5.10 | Nanocrystals |
| 15 | 1:1.5 | 69 | 0 | 0 | 4.45 | Microparticles |

References: The contents of the entirety of each of which are incorporated by this reference.

Albisetti C J, Castle J E. (1990) Dispersions of Chitin and Product Therefrom. U.S. Pat. No. 4,931,551 issued Jun. 5, 1990.

Azzaroni O, Moya S, Farhan T, Brown A A, Huck W T S. (2005) Switching the properties of polyelectrolyte brushes via "hydrophobic collapse." *Macromolecules.* 38, 10192-10199.

Baxter A, Dillon M, Taylor K D A, Roberts G A F. (1992) Improved method for i.r. determination of the degree of N-acetylation of chitosan. *Int. J. Biol. Macro.* 14, 166-169.

Càrdenas G, Cabrera G, Taboada E, Miranda S P. (2004) Chitin characterization by SEM, FTIR, XRD, and 13C cross polarization/mass angle spinning NMR. *J Appl. Polym. Sci.* 93, 1876-1885.

Chvalun S N, Poljakov D K, Medvedeva E A, Blekvell D. (2005) Nanocomposite and Method of Its Production. Abstract of Russian Patent Publication RU 2256601 published Jul. 20, 2005.

Fan Y, Saito T, Isogai A. (2008) Chitin nanocrystals prepared by TEMPO-mediated oxidation of α-chitin. *Biomacromolecules.* 9, 192-198.

Goodrich J D, Winter W T. (2007) α-Chitin nanocrystals prepared from shrimp shells and their specific surface area measurement. *Biomacromolecules.* 8, 252-257.

Habibi Y, Chanzy H, Vignon M. (2006) TEMPO-mediated surface oxidation of cellulose whiskers. *Cellulose.* 13, 679-687.

He X, Male K B, Nesterenko P N, Brabazon D, Paull B, Luong J H T. (2013) Adsorption and desorption of methylene blue on porous carbon monoliths and nanocrystalline cellulose. *ACS Appl. Mater. Interfaces.* 5, 8796-8804.

Heath L, Zhu L-F, Thielemans W. (2013) Chitin nanowhisker aerogels. *ChemSusChem.* 6, 537-544.

Jang M-K, Kong BG, Jeong Y-I, Lee CH, Nah J W. (2004) Physicochemical characterization of α-chitin, β-chitin, and γ-chitin separated from natural resources. *J. Polymer Science Part A: Polymer Chem.* 42, 3423-3432.

Lam E, Male K B, Chong J H, Leung A C W, Luong, J H T. (2012) Applications of functionalized and nanoparticle-modified nanocrystalline cellulose. *Trends in Biotechnol.* 30, 283-290.

Lam E, Leung A C W, Liu Y, Majid E, Hrapovic S, Male K B, Luong J H T. (2013) Green strategy guided by Raman spectroscopy for the synthesis of ammonium carboxylated nanocrystalline cellulose and the recovery of byproducts. *ACS Sustainable Chem. Eng.* 1, 278-283.

Langmuir I J. (1918) The adsorption of gases on the plane surfaces of glass, mica and platinum. *J. Am. Chem. Soc.* 40, 1361-1403.

Lavall R L, Assis O B G, Campana-Filho S P. (2007) β-Chitin from the pens of Loligo sp: Extraction and characterization. *Bioresour. Technol.* 98, 2465-2472.

Leung A C W, Hrapovic S, Lam E, Liu Y, Male K B, Mahmoud K A, Luong J H T. (2011) Characteristics and properties of carboxylated cellulose nanocrystals prepared from a novel one-step procedure. *Small.* 7, 302-305.

Leung C W, Luong J H T, Hrapovic S, Lam E, Liu Y, Male K B, Mahmoud K, Rho D. (2012) Cellulose Nanocrystals from Renewable Biomass. United States Patent Publication US 2012/0244357 published Sep. 27, 2012.

Leung A C W, Lam E, Chong J, Hrapovic S, Luong J H T. (2013) Reinforced plastics and aerogels by nanocrystalline cellulose. *J. Nanopart. Res.* 15, 1636.

Li J, Revol J-F, Marchessault R H. (1997) Effect of degree of deacetylation of chitin on the properties of chitin crystallites. *J. Appl. Polym. Sci.* 65, 373.

Male K B, Leung A C W, Montes J, Kamen A, Luong J H T. (2012) Probing inhibitory effects of nanocrystalline cellulose: Inhibition versus surface charge. *Nanoscale.* 4, 1373-1379.

Nair K G, Dufresne A. (2003) Crab shell chitin whisker reinforced natural rubber nanocomposites. 1. Processing and swelling behavior. *Biomacromolecules.* 4, 657-665.

Raabe D, Romano P, Sachs C, Fabritius H, Al-Sawalmih A, Yi S B, Servos G, Hartwig H G. (2006) Microstructure and crystallographic texture of the chitin-protein network in the biological composite material of the exoskeleton of the lobster Homarus americanus. *Mater. Sci. Engin. A.* 421, 143-153.

Revol J-F, Marchessault R H. (1993) In vitro chiral nematic ordering of chitin crystallites. *Int. J. Biol. Macromo.* 15, 329-335.

Shigemasa Y, Matsuura H, Sashiwa H, Saimoto H. (1996) Evaluation of different absorbance ratios from infrared spectroscopy for analyzing the degree of deacetylation in chitin. *Int. J. Biol. Macro.* 18, 237-242.

Tomoji T. (1984) Surface Treatment of Metal Without Causing Environmental Pollution. Japanese Patent Publication JP S59113185 published Jun. 29, 1984.

Zhang Y, Xue C, Xue Y, Gao R, Zhang X. (2005) Determination of the degree of deacetylation of chitin and chitosan by X-ray powder diffraction. *Carb. Res.* 340, 1914-1917.

The novel features will become apparent to those of skill in the art upon examination of the description. It should be understood, however, that the scope of the claims should not be limited by the embodiments, but should be given the broadest interpretation consistent with the wording of the claims and the specification as a whole.

The invention claimed is:

1. A process for producing chitin nanocrystals (ChNCs) comprising contacting a chitinous material with a sufficient amount of an inorganic persulfate to produce chitin nanocrystals from the chitinous material.

2. The process according to claim 1, further comprising providing the chitinous material to be contacted with the inorganic persulfate and recovering the chitin nanocrystals after contacting the chitinous material with the inorganic persulfate.

3. The process according to claim 1, wherein the inorganic persulfate comprises ammonium persulfate, sodium persulfate, potassium persulfate or a mixture thereof.

4. The process according to claim 1, wherein the chitinous material comprises non-vegetative biomass.

5. The process according to claim 1, wherein the chitinous material comprises crustaceans, fungi, mushrooms, insects or mixtures thereof.

6. The process according to claim 1, wherein the chitinous material comprises shrimp, crab, lobster and mixtures thereof.

7. The process according to claim 1, wherein the inorganic persulfate is contacted with the chitinous material at a temperature in a range of 45-80° C.

8. The process according to claim 1, wherein the persulfate is provided in an aqueous solution having a concentration of persulfate in a range of from 0.5 M to 2.0 M.

9. The process according to claim 1, wherein the chitinous material and the inorganic persulfate are contacted in amounts to provide a ratio of chitin to inorganic persulfate in a range of 1:2 to 1:5.

10. The process according to claim 1, wherein the persulfate is stirred with the chitinous material for a period of time in a range of from 6 hours to 24 hours.

11. The process according to claim 1 performed at a pH of 4 or less.

12. The process according to claim 1, wherein contacting the chitinous material with an inorganic persulfate is performed at about 60° C., the persulfate is provided in an aqueous solution at a pH of 4 or less having a concentration of persulfate of about 1.0 M, and the persulfate is stirred with the chitinous material for about 12 hours.

13. The process according to claim 1, further comprising deacetylating the chitin nanocrystals.

14. A chitin-based material comprising nanocrystals of chitin produced by the process of claim 1, the nanocrystals having surface carboxylic acid groups.

15. The chitin-based material according to claim 14, wherein the nanocrystals have a degree of oxidation in a range of from 0.04 to 0.20.

16. The chitin-based material according to claim 14, wherein the nanocrystals are selectively oxidized at C6 primary hydroxyl groups.

17. The chitin-based material according to claim 14, wherein the nanocrystals comprise an average width of 3-10 nm and an aspect ratio of 10 or greater.

18. The chitin-based material according to claim 14, wherein the nanocrystals are deacetylated to a degree of deacetylation of 15-65%.

19. The chitin-based material according to claim 14, wherein the nanocrystals have a crystallinity index at least 3% greater than the crystallinity index of a chitinous material from which the nanocrystals are made and a crystallinity index of 89% or greater.

20. The process according to claim 1, wherein the chitinous material comprises crustaceans.

* * * * *